(12) United States Patent  
Sloan

(10) Patent No.: US 8,582,421 B2  
(45) Date of Patent: Nov. 12, 2013

(54) ANALYZING WIRELESS COMMUNICATION DEGRADATION THROUGH COMPARISON OF COMMUNICATION LINKS

(75) Inventor: Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 510 days.

(21) Appl. No.: 12/878,882

(22) Filed: Sep. 9, 2010

(65) Prior Publication Data

US 2011/0058485 A1    Mar. 10, 2011

Related U.S. Application Data

(60) Provisional application No. 61/241,005, filed on Sep. 9, 2009.

(51) Int. Cl.
| | |
|---|---|
| *G01R 31/08* | (2006.01) |
| *G06F 11/00* | (2006.01) |
| *H04L 12/26* | (2006.01) |
| *G06F 15/173* | (2006.01) |

(52) U.S. Cl.
USPC ........... 370/216; 370/242; 370/246; 370/252; 709/223

(58) Field of Classification Search
USPC ................. 370/216–228, 230–238, 241–252; 709/208–211, 217–219, 223–226, 709/238–247
See application file for complete search history.

(56) References Cited

U.S. PATENT DOCUMENTS

| | | | |
|---|---|---|---|
| 5,867,103 A | 2/1999 | Taylor, Jr. | |
| 6,516,352 B1 * | 2/2003 | Booth et al. | 709/250 |
| 6,604,212 B2 * | 8/2003 | Sekizawa | 714/47.2 |
| 7,054,594 B2 | 5/2006 | Bloch et al. | |
| 7,593,972 B2 * | 9/2009 | Silva-Craig et al. | 1/1 |
| 8,369,286 B2 * | 2/2013 | Hamabe et al. | 370/332 |
| 8,433,319 B2 * | 4/2013 | Ren et al. | 455/436 |
| 2005/0182306 A1 * | 8/2005 | Sloan | 600/300 |
| 2007/0152811 A1 | 7/2007 | Anderson | |
| 2008/0255434 A1 | 10/2008 | Hayter et al. | |

* cited by examiner

*Primary Examiner* — Tri H Phan
(74) *Attorney, Agent, or Firm* — Thomas A. Runk; Fulwider Patton LLP

(57) ABSTRACT

A system and method of processing information regarding medical devices in wireless communication with each other is provided in which a handheld device has a first wireless communication link with a first medical device, such as a glucose sensor, and a second wireless communication link with a second medical device, such as an insulin pump. A processor in the handheld device monitors the status of the first and second wireless links and upon noting a change in status of either one, compares the first wireless link status with the second wireless link status and provides guidance for resolving a communication problem based on the comparison. The latency of the medical devices is considered as well as the ability to make system status changes, extend time periods before alarms are issued, and the characteristics of the medical devices are considered.

21 Claims, 6 Drawing Sheets

| | C1 | C2 | C3 | C4 |
|---|---|---|---|---|
| | Normal | Intermittent | None, short duration | None, Long duration |
| R1 Normal | Both devices in range | User is moving in and out of range, 10-20ft. | Nav and controller are together. Alarm (4) | Nav and controller are together. Alarm |
| R2 Intermittent | User is moving in and out of range | User is moving in and out of range. | Nav and controller are together. No alarm, wait (4) | Nav and controller are together. Alarm |
| R3 None, short duration | Pump and controller are together, off body. No alarm, wait. (1) | Pump and controller are together, off body. No alarm, wait. (1) | Controller out of range of both. No alarm, wait (5) | Controller out of range of both. Alarm |
| R4 None, Long duration | Pump and controller are together, off body. Alarm (2) | Pump and controller are together, off body. Alarm (2) | Controller out of range of both. Alarm | Controller has been left behind. (3) |

FIG. 7

ANALYZING WIRELESS COMMUNICATION DEGRADATION THROUGH COMPARISON OF COMMUNICATION LINKS

CROSS-REFERENCES TO RELATED APPLICATIONS

This application claims the benefit of U.S. Provisional Application No. 61/241,005, filed Sep. 9, 2009, incorporated by reference in its entirety.

BACKGROUND

The present invention relates generally to wireless communications, and more particularly, to monitoring the wireless link status of multiple wireless communication units to determine a reason for link degradation.

In some cases, medical device systems for disease management include sensor devices, medication delivery devices, processors, and/or control devices that operate together to assist a patient in maintaining healthier physiological processes. For example, in an integrated diabetes mellitus management (IDM) system, a sensor is attached at one position on a patient's body for the purpose of sensing the patient's glucose and providing a measurement signal representative thereof. An insulin pump is attached at a second position on a patient's body for the purpose of delivering programmed amounts of insulin to the patient for closely controlling the patient's glucose level. A third device, a controller, is typically a hand-held device that is configured to receive the glucose measurement signal, analyze it, and display a recommended dose of insulin to the patient. The patient may then control the insulin pump to deliver that recommended dose. In some cases, the delivery pump is configured to provide data signals regarding past and ongoing medication deliveries and the controller is also programmed to analyze such pump delivery data signals in determining the recommended dose of insulin provided to the patient.

Depending on the user, receipt and analysis of such sensor and pump data may need to occur on a continuous basis to avoid user health problems. For example, a user with diabetes should continually receive such data to be able to take steps to avoid a hypoglycemic or hyperglycemic condition, both of which can have serious consequences for the health of the user.

With the availability of low cost wireless technology, integrated systems such as that discussed above become more convenient and acceptable in that wires are not needed to interconnect the devices. Not only are wires burdensome to handle with on-body medical devices, but many users desire to keep their medical affliction confidential, which is more difficult to accomplish when wires exist. Each of the devices of the integrated system may incorporate a wireless communication module that allows it to communicate with at least one other device that uses a wireless link. In some cases, the communication module of the device may be a transceiver, but in other cases, it may simply be a receiver or a transmitter, depending on the function of the device.

Another important consideration with wireless radio frequency (RF) devices is their reliance on battery power. As is well known, transmitters typically tend to use far more battery power than receivers use. Different types of transmitting protocols may be employed that use less power, such as burst transmission, or periodic transmission, as opposed to continuous transmission. Nevertheless, battery power is still required and overuse of battery power can cause the premature expiration of the battery with the resulting requirement that the battery in the subsystem be replaced, or the entire device replaced. In an IDM system such as that discussed above, premature replacement of either the battery or the device itself is highly undesirable due to the necessary skin punctures that are required.

Referring now to FIG. 1, an IDM system 48 is shown. A glucose sensor 54 provides glucose signals while the pump 64 provides medication delivery data and pump status (such as programming) signals. Should both devices wirelessly transmit their data simultaneously, interference may result and the data may be lost since a receiver 70 may not reliably be able to discern between the two. One method of avoiding interference between the two is to use two different frequencies. In the embodiment shown in FIG. 1, the sensor-to-controller wireless RF link 50 would be a first subsystem 52 operating on a first frequency $f_1$ while the pump-to-controller wireless RF link 60 would be a second subsystem 62 operating on a second frequency $f_2$, that is different from the first frequency.

An example of a medical system using multiple frequencies in its subsystems is the integrated diabetes management (IDM) system being discussed and shown in FIG. 1. In one embodiment, the glucose sensor device 54 operates on 433 MHz, which is $f_1$. The insulin delivery pump 64 operates on 2.4 GHz, which is $f_2$. Due to the large difference between these two subsystem frequencies, interference is unlikely and better data communication is achieved. However, poor radio performance can nevertheless occur.

In the past, a radio subsystem that detects the existence of a degraded wireless link would increase the transmitting power to try to establish and maintain communications. However, this will have the effect of faster depletion of the battery as discussed above and may make the premature replacement of a device undesirably necessary. Maintaining a lower use of battery power to prolong the battery life of the devices is highly desired.

In prior systems, if the radio performance was degraded below a usability threshold, the user was informed and given general guidance to resolve the problem. Such general guidance may have taken the form of asking the user to determine general conditions of a device, such as checking that a switch is in the "on" position, or to check the batteries for viability, both of which are things that most users would have already considered. Other, more specific guidance was not provided, and present systems are unable to provide helpful information or guidance specifically regarding resolution of wireless communication issues when radio performance is degraded. Existing controllers, for example, typically instruct transmitter modules to switch to a continuous transmission mode in an attempt to establish a usable wireless link, or to increase the power level of transmission, both of which are undesirable if they are not absolutely needed. Other systems simply advise a user that a communication problem exists and that manual glucose testing, calculation, and pump analysis should be performed. The above techniques can result in considerable user inconvenience and anxiety, especially if the reason for the communication link degradation is easily correctable.

Hence, those skilled in the art have recognized the need for a system that is able to provide better guidance for correcting wireless communication problems without invoking the excessive use of battery power. A need has also been recognized for devices and systems that can provide improved diagnosis of wireless communication link problems and that can provide guidance that is more specific to users regarding correction of wireless communication problems between medical devices. The invention fulfills these needs and others.

SUMMARY OF THE INVENTION

Briefly and in general terms, the invention is directed to monitoring the status of communication links among multiple medical devices and comparing the status of those links to provide guidance to resolve communication link problems. The invention provides a system of processing information regarding medical devices in wireless communication with each other, the system comprising a base device having a first wireless communication link with a first medical device and a second wireless communication link with a second medical device, and the base device having a processor configured to monitor the status of the first wireless link and the status of the second wireless link, wherein the base device processor is further configured to determine if a problem exists with one or more of the first and second links, and wherein the base processor is further configured to compare the first wireless link status with the second wireless link status in the event that a problem with one or more of the monitored links is detected, and to provide guidance for resolving the problem based on the comparison.

In more detailed aspects, the processor is further configured to display the guidance on a visual display. The processor is further configured to determine that a link problem does not exist if the monitored link status lies within a latency of the respective medical device. The processor is further configured to cause a system change to occur based on the comparison. The processor is further configured to control the base device to cease monitoring a link based on the comparison, whereby power of the base unit is conserved.

In other detailed aspects, the processor is further configured to make a determination of link status based on a selected time period and on at least one characteristic of the respective medical device. The processor is further configured to issue an alarm based on the comparison and the selected time period. The processor is further configured to extend the time period based on the comparison, before an alarm is provided. The processor is further configured to determine the status of at least one of the medical devices based on the link comparison. Additionally, the processor is further configured to monitor the communication links to identify the existence of an intermittent communication link, and to consider the intermittent link in the comparison.

In yet other aspects, each of the medical devices are battery powered and the base station comprises a handheld battery-powered device, and the processor is further configured to initiate a system status change based at least in part on conserving battery power.

In accordance with the invention, there is provided a method of processing information regarding a base station having a first wireless communication link with a first medical device and having a second wireless communication link with a second medical device, the method comprising monitoring each communication link, detecting a problem in at least one of the communication links being monitored, determining if a problem exists with one or more of the monitored communication links, comparing the status of the monitored communication links with each other in the event that a problem appears to exist with one of the communication links, and providing guidance based on the link comparison for resolving the problem.

In more detailed aspects, the method further comprising displaying the guidance on a visual display. The method further comprising determining that a link problem does not exist if the monitored link status lies within a latency of the respective medical device. The method further comprising changing the system status based on the comparison. The method further comprising controlling the base device to cease monitoring a link based on the comparison, whereby power of the base unit is conserved.

In other more detailed aspects, the method further comprising making a determination of link status based on a selected time period and on at least one characteristic of the respective medical device. The method further comprising issuing an alarm based on the comparison and the selected time period. The method further comprising extending the time period based on the comparison, before an alarm is provided. The method further comprising determining the status of at least one of the medical devices based on the link comparison. The method further comprising monitoring the communication links to identify the existence of an intermittent communication link, and considering the intermittent link in the comparison.

Further features and/or variations of the invention may be provided in addition to those set forth herein. For example, the present invention may be directed to various combinations and subcombinations of the disclosed features and/or combinations and subcombinations of several further features disclosed below in the detailed description.

BRIEF DESCRIPTION OF THE DRAWINGS

The accompanying drawings, which constitute a part of this specification, illustrate various embodiments and aspects of the present invention and, together with the description, explain the principles of the invention. In the drawings:

FIG. 7 is a chart illustrating how the status of multiple links can be combined to infer guidance for correcting communication problems, consistent with aspects of the invention.

DETAILED DESCRIPTION OF THE PREFERRED EMBODIMENTS

Figure 1:
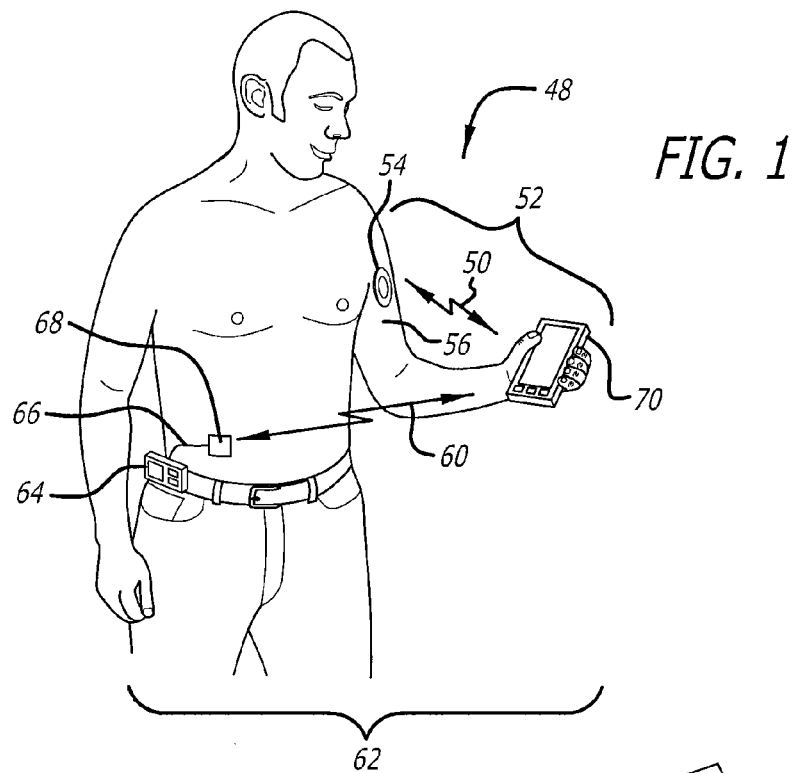
FIG. 1 is a diagram of a user having an integrated diabetes management system such as that described above, in which a pump and a glucose sensor are attached to separate body locations while a hand-held controller is used to receive data from both and provide the user with relevant information and recommendations for diabetes management, as well as alarms.

As described in further detail below, in accordance with embodiments of the present invention, there is provided a system and method for facilitating data processing and control for use in a medical telemetry system, and in particular for analyzing wireless communication degradation. In particular, the status of multiple wireless links are compared to determine the cause for signal degradation and for providing the user with guidance for correcting communication problems. A system and method of facilitating data communication and/or control aspects for use in medical telemetry systems such as, for example, in continuous glucose monitoring subsystems, medication delivery subsystems, and others are described. The embodiments set forth in the following description and in the drawings do not represent all embodiments consistent with the claimed invention. Instead, they are merely examples consistent with certain aspects related to the invention. Wherever possible, like reference numerals will be used throughout the drawings to refer to the same or to like elements.

Referring again briefly to FIG. 1, an integrated diabetes management system 48 is shown that includes a glucose sensor 54 mounted to a user's upper arm 56. The glucose sensor may take the form of a continuous glucose sensor that punctures the user's skin and wirelessly transmits data representative of the sensed glucose level of the user. Transmission may occur every few milliseconds or may only occur only once per minute depending on the glucose sensor used. A sensor of this type is available from Abbott Diabetes Care Inc., Alameda, Calif., under the name of the Freestyle Navigator® sensor.

An insulin delivery pump 64 forms part of the IDM system 48 and is also wireless. In FIG. 1, it is mounted to a user's waist band and has tubing 66 leading to an injection site 68. The injection site includes a cannula that punctures the user's skin to deliver a medication, such as insulin. However, other configurations are possible. In another configuration, the insulin pump 64 has a self-contained injection cannula and the entire pump is mounted to a user's injection site by adhesive. The injection cannula is extended to puncture the user's skin for the delivery of insulin. Control over the extension of the cannula to puncture the user's skin may be exercised by wireless command from the hand held controller 70, in such an embodiment.

The wireless communication link 60 may be used to receive insulin delivery status and other data from the pump 64, and may be used to control the pump, such as by triggering insertion of the delivery cannula as described above. A representative insulin delivery pump of this type is the Omni-Pod® Pod pump from the Insulet Corporation, in Bedford, Mass.

The remote controller 70 communicates with both the sensor 54 and with the pump 64. To do so, the remote controller includes two transceivers in this embodiment. In one embodiment, the controller 70 receives the sensor data but also can query the sensor 54 for further data, thereby acting as a transceiver. In an embodiment, the controller 70 not only receives pump data from the pump 64, but also can query the pump or provide commands to the pump, as discussed above. The controller 70 also therefore has a transceiver for communicating with the pump. Pump data may include the quantity of insulin already delivered as well as a time frame reference so that the controller 70 can determine "insulin-on-board." Pump data may also include the quantity of insulin already programmed for future delivery as well as the time frame. The controller analyzes this information in formulating a recommendation to the user to increase insulin delivery, decrease insulin delivery, or continue with the insulin delivery as programmed.

To avoid interference in RF communications as discussed in the Background section above, the wireless sensor 54 transmits and receives at an RF frequency of 433 MHz while the delivery pump 64 transmits and receives at an RF frequency of 2.4 GHz in this embodiment. Frequencies differing greatly from those may be used in another embodiment. Because the remote controller 70 interfaces with both the sensor 54 and the pump 64, it includes two transceiver modules, one of which operates on one of the above frequencies and the other of which operates on the other frequency. These are referred to herein as the sensor subsystem 52 and the pump subsystem 62. This is not meant to be restrictive in that other types of subsystems or overall systems having different operational frequencies apply as well. Each of these radio subsystems operates independently and each of the radio frequencies or bands has unique characteristics. For example, the operating range, types of interferers, propagation characteristics, and latency of each subsystem is different in this embodiment. The differences between each radio subsystem's performance characteristics and the combined resulting behaviors can be used to characterize the operating environment.

For each radio subsystem 52 and 62, there are conditions that prevent or degrade their communications link 50 and 60 respectively, such as distance, antenna orientation, intervening objects, and co-channel interference. When the respective devices 54 and 64 cannot communicate with the remote controller 70, the remote controller, without more information, cannot determine the exact cause. By combining information about the performance of two (or more) radio links, the controller can possibly determine the cause and the user can be given more specific guidance on how to resolve the problem that is causing communication link degradation.

Figure 2:
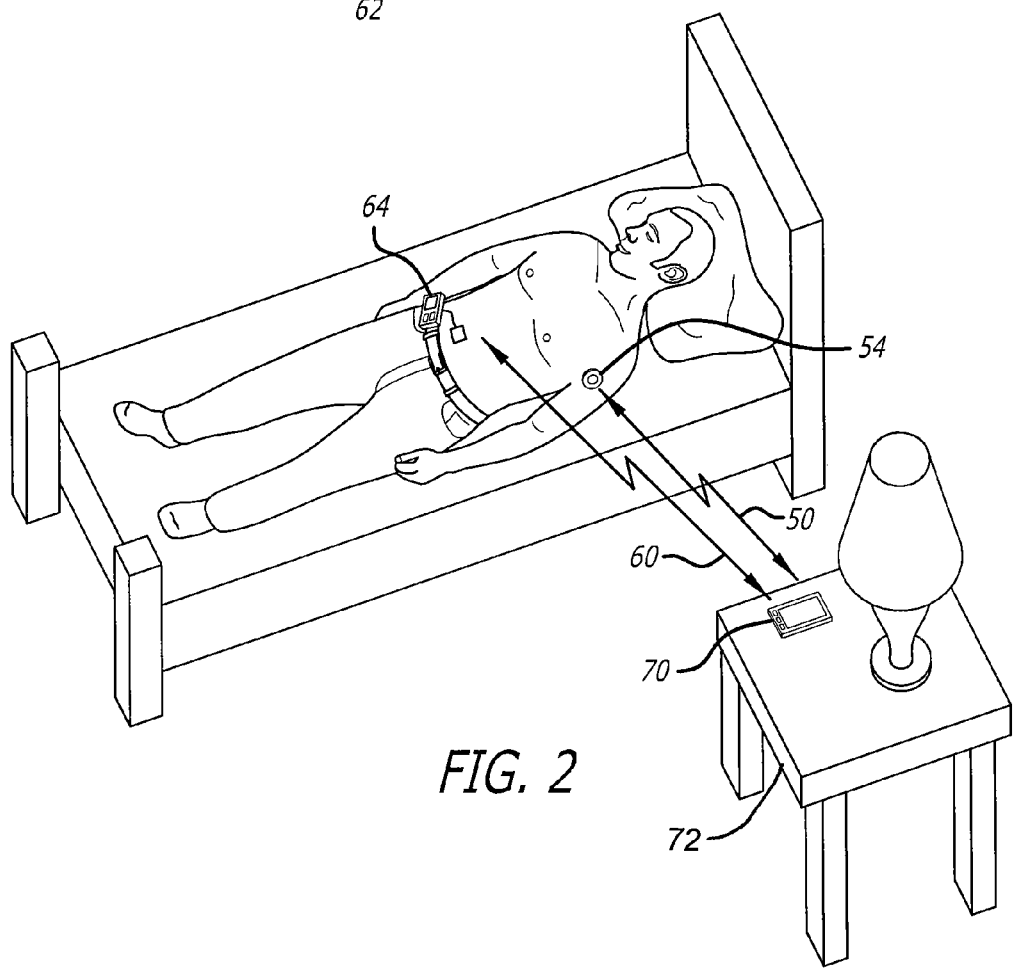
FIG. 2 is a diagram showing a sleeping user with an integrated diabetes management system monitoring glucose levels and transmitting pump status data, with the controller placed on a bedside table removed from the patient.

Referring to FIG. 2, the user is sleeping with the controller 70 placed at a distance on a nightstand 72. The controller is programmed to issue audible, vibratory, and visual alarms when certain glucose conditions of the user occur in this embodiment. Also in this embodiment, the IDM system 48 is using a continuous sensor 54 and a programmed delivery pump 64. The controller 70 expects to wirelessly receive data from both devices regularly so that the user's glucose condition may be monitored. Should the wireless data flow from one or more of the sensor device or the delivery pump be interrupted due to a degradation in a communication link or links, the controller 70 may sound an audible and/or vibratory alarm to awaken the patient. In accordance with aspects of the invention, the controller will also provide information to the patient regarding the faulty communication link. The patient may then take steps to remedy the problem.

In accordance with aspects of the invention, the status of both RF links of the two radio subsystems 52 and 62 (FIG. 1) can be compared in an effort to reach some conclusion about the cause of degraded or no performance. Perhaps in the simplest case, a communication link analysis program run by the controller 70 would review the signal strength of each device's wireless link 50 and 60 to the controller. In finding that both links are nonexistent, the controller could determine that the remote controller is out of range of the user, the remote controller is off, or the battery is depleted. Such an occurrence could arise if the user left the remote controller in another part of the house before retiring. The controller would issue a loud audible alarm to attract the user's attention. The user may then retrieve the controller and place it within range of the medical devices 54 and 64.

In the one embodiment, the RF subsystem 62 (FIG. 1) between the pump 64 and the controller 70 would be operating at 2.4 GHz. While the transmission range at this frequency can be around 100 meters (several hundred feet), the need to conserve battery power dictates that the transmission range be limited to approximately one to two meters (three to seven feet). This frequency in the medical field is considered to have a "shorter" range. The RF subsystem 52 between the sensor 54 and the controller would be operating at 433 MHz. This frequency has a transmission range (at reduced power to conserve battery power) of approximately 30.5 meters (100 feet), which is considered to be a "longer" range. It has also been observed that both frequencies are susceptible to interference from various objects. At 2.4 GHz, the human body can provide significant interference. In FIG. 2, the pump 64, which operates wirelessly at 2.4 GHz, is located on the far side of the user from the controller 70. The user's body could provide significant interference to the communication link 60 if he were to roll to his right. However, the user's body would not significantly interfere with the operating frequency of the sensor 54 at 433 MHz. One reason is that the user's body is not disposed between the sensor and the controller 70, and another reason is that the user's body does not provide significant interference at that frequency.

Another characteristic of the two different frequencies of operation is that the 433 MHz subsystem has a lesser signal latency than the 2.4 GHz subsystem. The term "latency" or "signal latency" as used herein is generally meant to mean the time between transmissions of a device. Thus if a glucose sensor 54 transmits only once per minute, it has a latency of a minute. Transmission at such a low rate is possible due to the need to conserve battery power so that the sensor can remain on the user's arm for a full three days.

Another example in which the controller 70 having a multiple radio-link analysis program running is when the longer-range subsystem 52 is able to communicate but the shorter range subsystem 62 is not. The program could then determine that the distance between the user and the remote controller 70 is likely somewhere between the two ranges of the RF links. A further example is the case where the longer latency subsystem cannot communicate, and the lower latency subsystem communication has been intermittent. The program would determine that the user is likely moving in and out of range of the medial devices with the remote control 70. Therefore by combining information about the performance or status of two or more radio links, the controller may be able to provide more useful information and guidance to the user to make adjustments so that the communication links are established and maintained in good working order.

Figure 3:
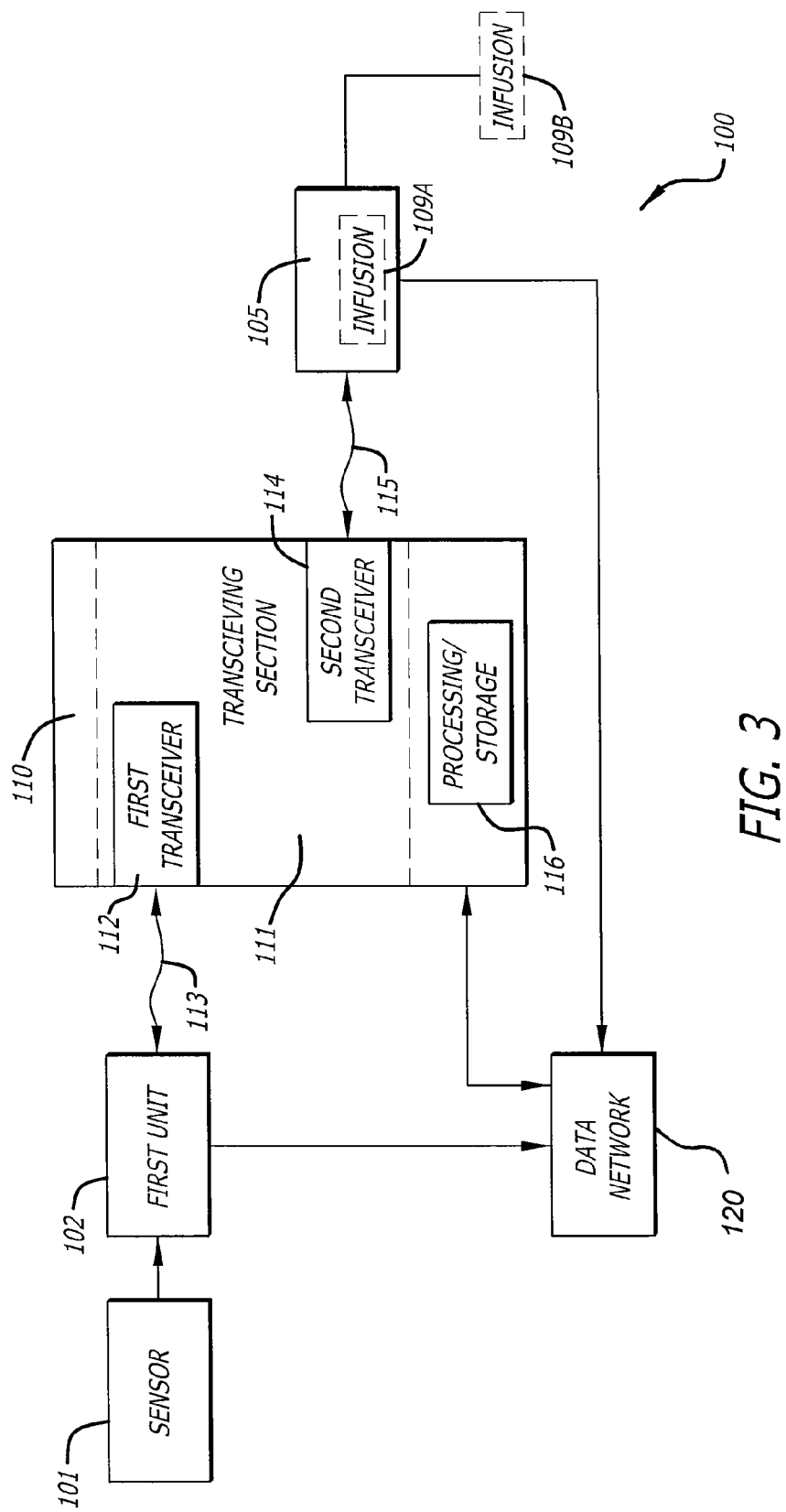
FIG. 3 is a block diagram of an exemplary dual-transceiver system consistent with certain aspects related to the innovations herein, in which one transceiver is used to produce the wireless link of the sensor and a second transceiver is used to produce the wireless link of the infusion delivery device.

FIG. 3 illustrates a data processing, monitoring and management system such as, for example, an integrated diabetes management (IDM) system 100 consistent with certain aspects of the invention. The subject innovations are further described primarily with respect to an analyte (e.g., glucose) monitoring and management system for convenience and such description is in no way intended to limit the scope of the invention. It is to be understood that the innovations herein are applicable to configurations related to the processing of data and the management of a variety of medical devices, and the monitoring of a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

Continuing to refer to FIG. 3, an exemplary data processing, monitoring, and management system 100 comprises a sensor 101, a first processing/transceiver unit 102 coupled to the sensor 101, a base processing unit 110, and a second processing/transceiver unit 105. The base unit 110 is configured to wirelessly communicate with the first processing/transceiver unit 102 via a first transceiver subsystem 112 over a first RF link 113, and with the second processing/transceiver unit 105 via a second transceiver subsystem 114 over a second RF link 115. The base unit 110 may be, for example, a portable or handheld computing component that serves as a remote management/control device such as the hand held controller 70 of FIGS. 1 and 2, and may include one or more subcomponents 116 for processing wireless communication data, and storing data or software such as applications enabling the innovations herein, among other things. For example, the base unit 110 may consist of, or include, a personal computer, a portable computing component such as a laptop or a handheld device (e.g., personal digital assistant (PDA), smart phone, etc.), and the like. Additionally, the base unit 110 and the other units 102 and 105 may further be connected to a data network 120 for storing, retrieving and updating data or programs, such as those associated with the innovations herein. This data network may comprise an internal facility network such as a local area network or a wide area network, the Internet, or other network. While various processing features throughout this disclosure may be illustrated as occurring in one particular unit, it should be understood that the functionality may be distributed among one or more of the processors within any suitable unit in the system 100.

According to certain implementations, the first and second processing/transceiver units 102 and 105 may be on-body devices associated with a glucose monitoring and insulin pumping devices used for management of a medical condition. In some illustrative systems, the first processing/transceiver unit 102 may be a component of a continuous glucose monitoring ("CGM") subsystem that is linked to the base unit 110 via the first wireless communications link 113, and the second processing/transceiver unit 105 may be a processing component of an insulin delivery pump subsystem that is linked to the base unit via second wireless communications link 115. In one embodiment, the sensor 101 may comprise the Freestyle Navigator® sensor and the first transceiver unit 102 may be integrated with that sensor, or may be a separate transceiver unit that electrically connects and mechanically couples to the sensor. The infusion device 109A may take the form of an insulin pump and the second transceiver 105 may be integrated within the housing of the pump as shown in box 105, or may have a separate housing 109B that electrically connects and mechanically couples to the pump as shown in dashed lines. Other configurations are possible.

In one illustrative embodiment, the IDM system 100 may include a CGM subsystem 102 that wirelessly communicates using 433 MHz signals, or 2.4 GHz or 315-322 MHz signals, or other, and the pump subsystem 105 that uses a different frequency, such as 2.4 GHz or 433 MHz, or other, signals. In general, methods and systems consistent with the innovations herein first determine information regarding a first status of the first wireless link 113 and a second status of the second wireless link 115, wherein various problems/issues associated with wireless communications or the links may also be identified. Then, based on the information determined, intelligence is provided to a user. This intelligence may include information regarding one or more of the devices (e.g., location, status, etc.) and/or diagnosis, guidance, or resolution regarding any of the problems/issues identified, among other things.

By way of one example, in the illustrative 433 Mhz/2.4 GHz subsystems mentioned above, exemplary methods and systems may first determine a transmission state or link status or condition for each subsystem. Various transmission states and link status or conditions are set forth throughout this disclosure and may include whether the link is operating normally, whether the link is operating intermittently, whether the link is nonexistent, the status of short range transmissions, and the status of long range transmissions, among other things. Once information regarding the status of each link is determined, methods and systems herein may process this information using logic keyed to the particular devices and transmission protocols involved, and then provide the user with feedback regarding one or more of the devices (e.g., location, status, etc.) and/or diagnosis and guidance for resolution of any problems/issues identified, among other things. Various examples of device-related feedback are set forth throughout this disclosure and may include whether or not a device is in range of a transceiver, whether a device in intermittently moving into/out of range, whether or not a user is within or outside of one or more specified ranges, etc.

In determining the status of a link, the system 100 also considers the latency characteristic of each subsystem. For example, when a device is programmed to transmit only once per minute, the device is not necessarily "intermittent" is no transmission has been received for forty-five seconds. The device's latency is considered in making a determination of whether or not transmissions from the device are being received "intermittently."

Hardware and/or software applications may be employed to enable the logic, keyed to the particular devices and transmission protocols, used by the method and system herein. For example, this logic may be implemented via a database as well as associated program code that allows access and utilization of data within the database. Such functionality may be installed in one or more of the devices or units, or it may be provided via wired or wireless connection, computer readable media download, or other suitable means. Such logic or database may include information regarding an interferer (e.g., objects that may interfere with communications, sources or causes of interference), a propagation characteristic (e.g., performance, signal data, frequency, signal strength), or a latency (e.g., temporal, and related aspects) of the communications between the units, and this information may be used in determining feedback for the user, such as device status or device location information, diagnosis of, guidance regarding, or a resolution of a wireless-communication-related problem. Various diagnoses, guidance, or resolution of identified issues/problems are set forth throughout this disclosure or inherently flow from the issue/problems identified and may include an "out of range" notification, a vicinity determination, a message regarding a device location or request to move a device, a message regarding verification of a transmission or device detail, a recommendation regarding adjusting a transmission or device detail, a message to check for and/or avoid one or more likely causes of interference, and a recommendation regarding a transmission or channel selection, among others.

In the exemplary implementation of FIG. 3, the first and second transceiver units 112 and 114 of the base unit 110 are shown as being wirelessly linked to their respective first and second units 102 and 105 for wireless data transmission. While shown as being separate and distinct in FIG. 3, the first transceiver unit 112 and the second transceiver unit 114 may, more generally, be embodied within a more unitary transceiving section 111 that utilizes or shares components or functionality between transceivers as appropriate. Moreover, while not shown, the first transceiver 112 may also be configured to communicate with the second unit 105, and the second transceiver 114 may also be configured to communication with the first unit 102. In another arrangement, each unit of the system may be configured for bi-directional wireless communication with any of the other units.

Only one sensor 101, first unit 102, base unit 110, and second unit 105 are shown in the exemplary implementation of the disease management/monitoring system 100 illustrated in FIG. 3. However, it will be appreciated by one of ordinary skill in the art that the system 100 may include one or more sensors 101, first units 102, base units 110, and second units 105. Moreover, within the scope of the present disclosure, the system 100 may include a continuous analyte monitoring system, or semi-continuous, or a discrete monitoring system. Further, in such multi-component environments, each device may be configured to be uniquely identified by each of the other devices in the system so that communication conflict is readily resolved between the various components within the system 100.

In one implementation of the present disclosure, the sensor 101 is physically positioned in or on the body of a user whose analyte level is being monitored. The sensor 101 is configured in one embodiment to continuously sample the analyte level of the user and convert the sampled analyte level into a corresponding data signal for transmission by the first unit 102 on a periodic basis. In one implementation, the first unit 102 is coupled to the sensor 101 so that both devices are positioned on the user's body, with at least a portion of the analyte sensor 101 positioned transcutaneously under the skin layer of the user. The first unit 102 may perform data processing such as filtering and encoding on data signals, each of which corresponds to a sampled analyte level of the user, for transmission to the base unit 110.

In one exemplary implementation, the system 100 may be configured as a one-way RF communication path from the first unit 102 to the base unit 110. In such implementation, the first unit 102 transmits the sampled data signals received from the sensor 101 without acknowledgement from the base unit 110 that the transmitted sampled data signals have been received. For example, the first unit 102 may be configured to transmit the encoded sampled data signals at a fixed rate (e.g., at one minute intervals) after the completion of the initial power-on procedure. Alternatively, the system 100 may be configured with a bi-directional RF (or otherwise) communication between the first unit 102 and the base unit 110.

The base unit 110 may include a data processing section 116 that is configured to process data such as that received from the first and second units 102 and 105 respectively. It may additionally process instructions regarding the other units. Additionally, in one aspect, an exemplary base unit 110 may also include an analog interface section that is configured to communicate with the first unit 102. In one implementation, the analog interface section may include an RF receiver and an antenna for receiving and amplifying the data signals from the first unit 102, which, thereafter, may be demodulated with a local oscillator and filtered through a band-pass filter.

In operation, the base unit 110 may be configured to detect the presence of the first unit 102 or the second unit 105 within its range as a function of, for example, the signal strength of the detected data signals received or from predetermined transmitter identification information. Upon successful synchronization with a corresponding unit 102 or 105, the base unit 110 may be configured to begin data receipt and processing, such as to begin receiving from the first unit 102 data signals corresponding to the user's detected analyte level, to transmit and receive data with the second unit 105 regarding infusion-related communications 109. For example, the base unit 110 in one implementation may be configured to perform synchronized time hopping with the corresponding synchronized first and/or second units via the respective communication links.

Within the scope of the present disclosure, as shown in FIG. 3, the second unit 105 may be coupled to an infusion device 109B, such as an insulin infusion pump or the like, which may be configured to administer insulin to patients, and which may be configured for communications with the base unit 110 to receive, among other things, data or instructions. The insulin delivery pump 105 may also be configured to forward data to the base unit 110 representative of insulin already delivered over a particular time frame and the remaining insulin to be delivered in accordance with current programming instructions. From this, insulin-on-board can be calculated by the base unit, and the effects of insulin to be delivered can be predicted. As a result, changes in insulin delivery may be calculated at the base unit 110. Alternatively, the second unit 105 may be configured to integrate an infusion device 109A therein so that the second unit 105 is configured to administer insulin therapy to patients, for example, for administering and modifying basal profiles, as well as for determining appropriate boluses for administration based on, among others, the detected analyte levels received from the first unit 102. Such medical techniques, i.e., boluses, basal rates, can also be employed by the separate device 109B.

The first unit 102, the base unit 110, and the second unit 105 may each be configured for bi-directional wireless communication such that each of the first unit 102, the base unit 110 and the second unit 105 may be configured to communicate (that is, transmit data to and receive data from) with each other via one or more wireless communication links in another embodiment. Further, the second unit 105 may in one implementation be configured to receive data directly from the first unit 102 via a communication link (not shown), which may be configured for bi-directional communication.

In some implementations, the first unit 102, base unit 110, and second unit 105 may be configured to wirelessly communicate via communication links including one or more of an RF communication protocol, an infrared communication protocol, a Bluetooth enabled communication protocol, an 802.11x wireless communication protocol, a Zigbee transmission protocol, or an equivalent wireless communication protocol which would allow secure, wireless communication of several units (for example, per HIPPA requirements) while avoiding potential data collision and interference. All of these are referred to as "wireless" herein.

Figure 4:
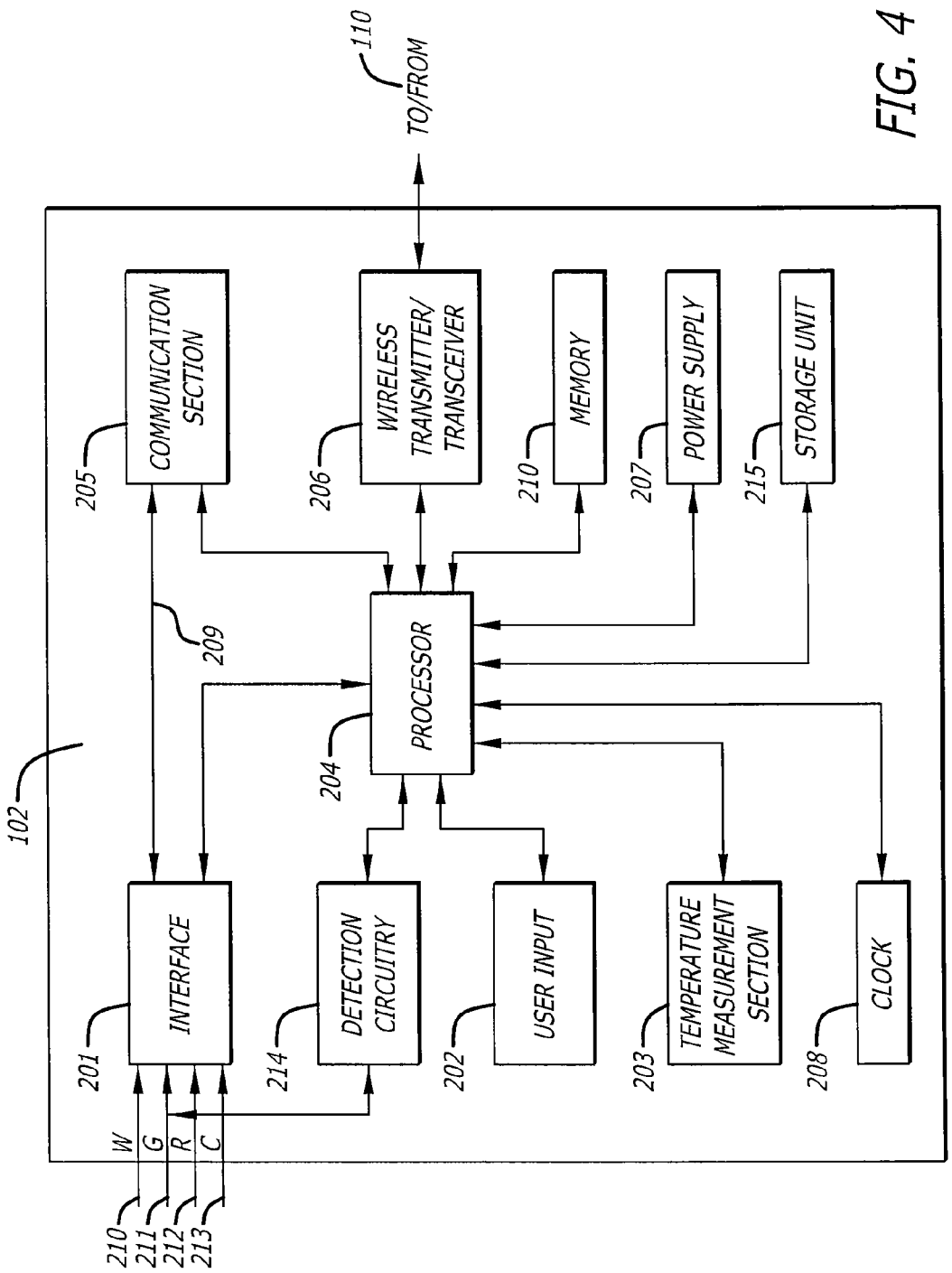
FIG. 4 is a block diagram of an exemplary first (analyte monitoring) unit consistent with certain aspects related to the innovations herein, that includes various components, two of which are a communication section and a transceiver.

FIG. 4 is a block diagram of an exemplary first unit 102 shown in FIG. 3 in accordance with one embodiment. The first unit 102 in one implementation may include an interface 201 configured to communicate with the sensor 101 (FIG. 1, W, G, R, and C being electrodes), a user input 202, and a temperature detection/measurement section 203, each of which is operatively coupled to a processor 204 such as a central processing unit (CPU). The user input may take many forms, such as a touch screen, keypad, keyboard, and others. Further shown in FIG. 4 are a communication section 205 and a wireless transceiver 206, each of which are also operatively coupled to the processor 204. Moreover, a power supply 207, such as a battery, is also provided in the first unit 102 to provide the necessary power for the first unit. Additionally, as can be seen from the FIG. 4, a clock 208 is provided to, among other things, supply real time information to the transmitter processor 204.

In one implementation, an input path is established from the sensor 101 (FIG. 1) and/or other suitable test or data component to the analog interface 201 of the first unit 102, while an output is established from the output of the transceiver 206 of the first unit 102 for transmission to the base unit 110. As such, via this path the first unit 102 is configured to transmit to the base unit 110 processed and/or encoded data signals received from the sensor 101 (FIG. 1).

As discussed above, the first unit processor 204 may be configured to transmit control signals to the various sections of the first unit 102 during the operation of the first unit. In one implementation, the processor 204 also includes a memory 210 for storing data such as the identification information for the first unit 102, as well as the data signals received from the sensor 101. The stored information may be retrieved from the memory and processed for transmission to the base unit 110 under the control of the processor 204. Furthermore, the power supply 207 may include a commercially available battery.

The first unit 102 is also configured such that power supplied from the power supply section 207 may be controlled via feedback received from the base unit 110. Specifically, the base unit 110 may transmit instructions for controlling the provision of power and the operation of the transceiver 206, to improve power management. For example, when the user is out of range of two wireless communications links, the base unit can save energy by using just one link instead of two to determine when they are back in range. The power supply may be reduced to a very low "sleep" mode output in such case, through instructions from the base unit 110 to the processor 204.

Typically, the power supply 207 is capable of providing power to the transmitter 206 for a minimum of about three months of continuous operation after having been stored for about eighteen months in a low-power or non-operating mode. In one implementation, this may be achieved by the processor 204 operating in low power modes in the non-operating state, for example, drawing no more than approximately 1 µA of current. Moreover, as shown in FIG. 4, while the power supply unit 207 is shown as connected with to the processor 204, and as such, the processor 204 is configured to provide control of the power supply unit 207, it should be noted that within the scope of the present disclosure, the power supply unit 207 may be also be directly connected to each of the other components 201, 214, 202, 203, 208, 205, 206, 210, and 215 in an embodiment to provide the necessary power to each of the components of the first unit 102 shown in FIG. 4. Additionally in another embodiment, the power supply 207 may have its own internal processor and programming to provide "smart" power control.

In some implementations, the power supply section 207 of the first unit 102 may include a rechargeable battery unit that may be recharged by a separate power supply recharging unit (for example, provided in the base unit 110) so that the first unit 102 may be powered for a longer period of usage time. Moreover, in one implementation, the first unit 102 may be configured without a battery in the power supply section 207, in which case the first unit 102 may be configured to receive power from an external power supply source (for example, a battery) as discussed in further detail below.

Referring further to FIG. 4, the temperature measurement section 203 of the first unit 102 maybe configured to monitor temperature(s) associated with the user, such as that of the skin near the sensor 101 (FIG. 3) insertion site. The temperature reading may be used by the processor to adjust the analyte readings obtained from the interface 201 or may simply be stored for possible analysis later. The transceiver 206 of the first unit 102 may be configured for operation in the frequency band of about 433 MHz, or other frequencies, such as 315 MHz to 322 MHz, for example. Further, in one implementation, the transceiver 206 is configured to modulate the carrier frequency by performing Frequency Shift Keying and Manchester encoding. In one implementation, the data transmission rate is 19,200 symbols per second, with a minimum transmission range for communication with the base unit 110.

Referring yet again to FIG. 4, also shown is a detection circuit 214 coupled to one or more electrodes (W, G, R, or C) of the sensor 101 (FIG. 3) and the processor 204 in the first unit 102. The detection circuit 214 in accordance with one implementation of the present disclosure may be configured to detect leakage current in the sensor 101 to determine whether the measured sensor data are corrupt or whether the measured data from the sensor 101 is accurate.

Additional data monitoring systems and devices consistent with the innovations herein are provided in U.S. Pat. No. 6,175,752 issued Jan. 16, 2001 entitled "Analyte Monitoring Device and Methods of Use", and in application Ser. No. 10/745,878 filed Dec. 26, 2003, publication No. US2004/0186365A1, entitled "Continuous Glucose Monitoring System and Methods of Use," each assigned to the Assignee of the present application, and each of which are incorporated herein by reference in entirety for all purposes.

Figure 5:
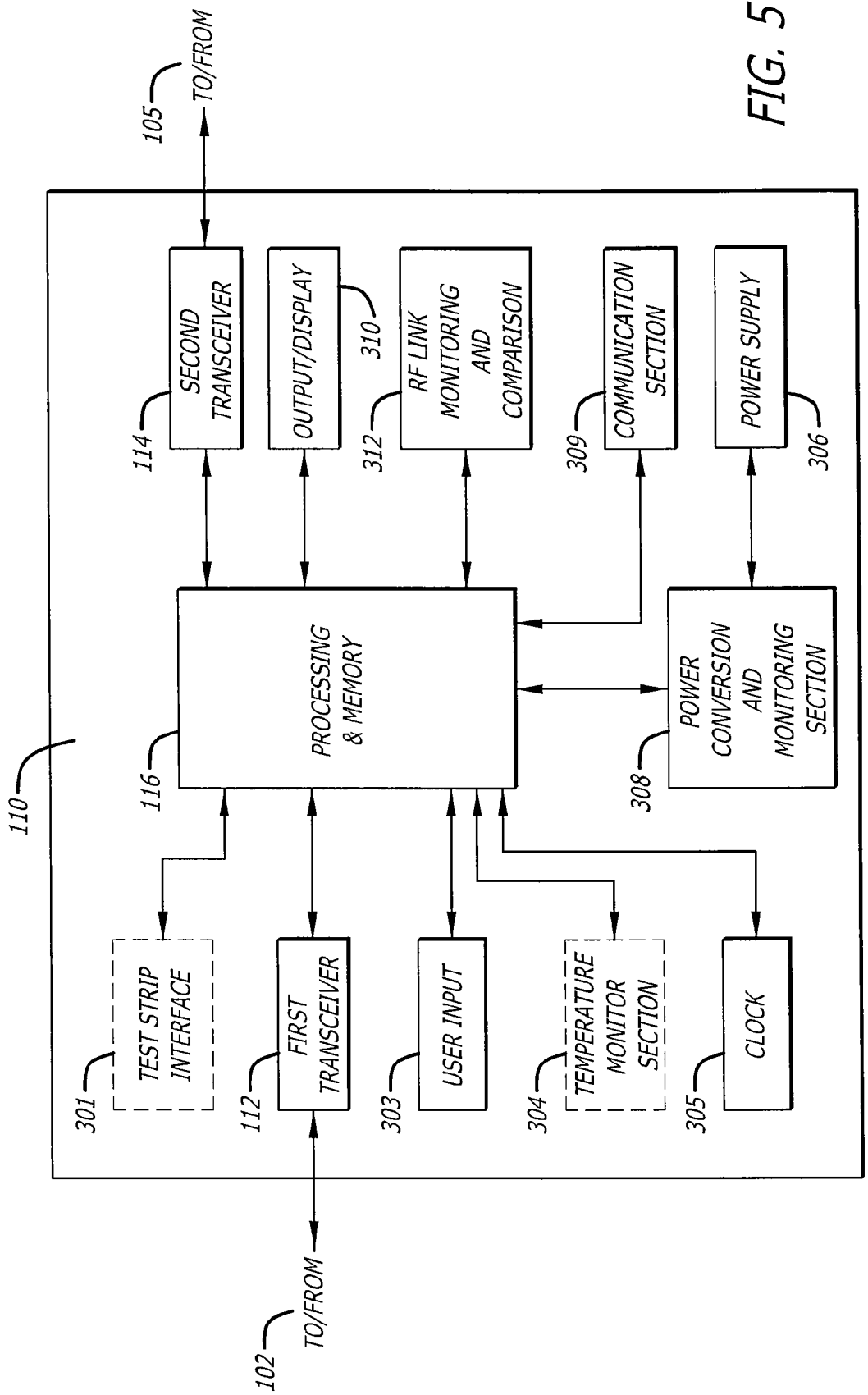
FIG. 5 is a block diagram of an exemplary base unit or hand held controller consistent with certain aspects related to the innovations herein, having first and second transceivers so that the status of both RF links can be monitored and analyzed, and a processor for running a link status, comparison, and user guidance program.

FIG. 5 is a block diagram of an exemplary base unit 110 of the system 100 shown in FIG. 3 consistent with aspects related to the innovations herein. Referring to FIG. 5, the base unit 110 may optionally include a blood glucose test strip interface or reader 301, a wireless first transceiver 112, a user input 303, a temperature monitoring section 304, and a clock 305, each of which is operatively coupled to the processor and memory component 116 (also referred to as just "processor"). As can be further seen from FIG. 5, the base unit 110 also includes a power supply 306 operatively coupled to a power conversion and monitoring section 308. Further, the power conversion and monitoring section 308 may also be coupled to the processor 116. Moreover, also shown are a second transceiver 114, and an output display 310, such as a visual display, audible signal generator, vibratory signal generator, and possibly others, which may each also be operatively coupled to the processor 116.

In one implementation, the test strip interface 301 may include a glucose level testing reader to receive a manual insertion of a glucose test strip, for determination, transmission, and/or display of the detected glucose level shown by the test strip on the output 310 of the base unit 110. This manual testing of glucose can be used to calibrate analyte sensing components, such as the sensor 101 (FIG. 3). The first wireless transceiver 112 may be configured to communicate with the transceiver 206 of the first unit 102, to receive encoded data signals from the first unit 102 for, inter alia, signal mixing, demodulation, and other data processing. The user input 303 of the base unit 110 is configured to allow the user to enter information into the base unit 110 as needed. In one aspect, the input 303 may include one or more keys of a keypad, a touch-sensitive screen, a voice-activated input command unit, or other means. The temperature measurement section 304 is configured to provide temperature information of the base unit 110 to the processor 116, while the clock 305 provides real time information to the processor 116.

Each of the various components of the base unit 110 shown in FIG. 5 is powered by the power supply 306 which, in one implementation, includes a battery. Further, the logic described herein may control provision of power and operation of the base unit 110, i.e., as a function of the innovations herein regarding communication link information, to improve power management. For example, the processor may execute or run programs to reduce the transmit power level, reduce the retry rate, idle all but one RF link, and rely on that one link to determine the link status. Additionally, the power conversion and monitoring section 308 may be configured to monitor the power usage by the various components in the base unit 110 for effective power management and to alert the user, for example, in the event of power usage that renders the base unit 110 in sub-optimal operating conditions. An example of such sub-optimal operating condition may include, for example, operating the transceiver at a full power level when the unit to which or from which communications are being sent or received is out of range, or using a vibration output mode for an excessive period of time thus substantially draining the power supply 306. Moreover, the power conversion and monitoring section 308 may additionally be configured to include a reverse polarity protection circuit such as a field effect transistor (FET) configured as a battery activated switch.

The second transceiver 114 in the base unit 110 may be configured to provide a bi-directional communication path from the testing and/or manufacturing equipment for, among others, initialization, testing, and configuration of the base unit 110. The communication section 309 can also be used to upload data to a network or other computer, such as time-stamped blood glucose data stored in the memory 116, or in real time. Such communication links may also be utilized to connect to networks, supervisory individuals or entities, healthcare providers, or the link. Communication links with external devices (not shown) can be made, for example, by cable, or wireless, such as by infrared (IR) or RF link. The output 310 of the base unit 110 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones or "smart" phones. In a further embodiment, the base unit 110 also includes an electro-luminescent lamp configured to provide backlighting to the output 310 for output visual display in dark ambient surroundings.

Although an RF link analysis program may be stored in the processor/memory unit 116, it is shown separately here in box 312. The processor 116 runs this program to determine the status of all RF links and to analyze those links when a wireless communication problem develops. Based on the analysis made by the RF link program 312, the processor 116 provides guidance to the user by means of the output 310 visually and/or audibly.

Figure 6:
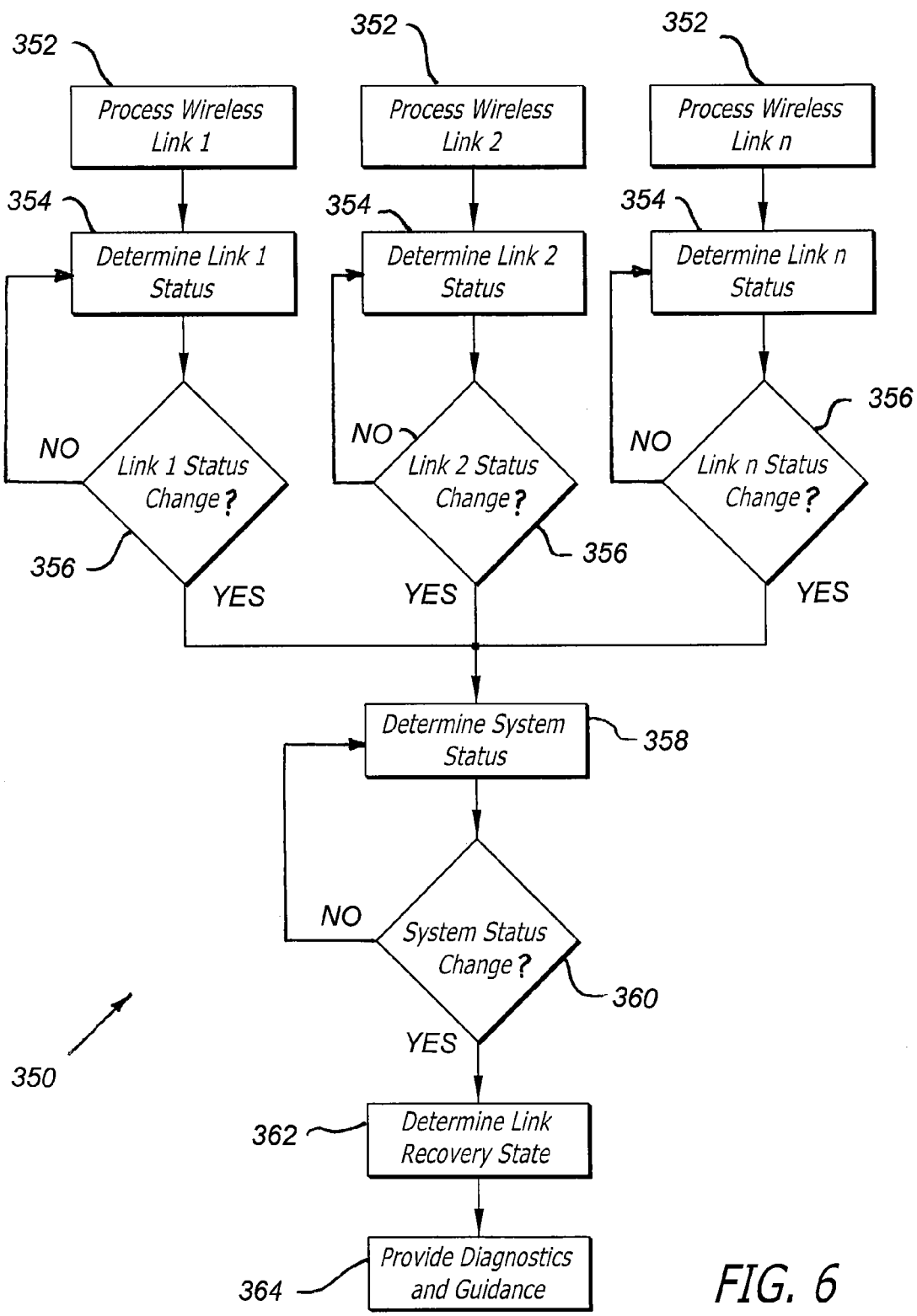
FIG. 6 is a flow diagram illustrating an exemplary method of wireless communication link monitoring and analysis showing Link 1, Link 2, and Link n (multiple links), as well as providing guidance to the user to resolve communication degradation problems.

FIG. 6 is a flow diagram illustrating an embodiment of a portion of a method in which the status of each of multiple wireless communication links is analyzed and compared to the status of the other links to identify a communication problem. Referring to FIG. 6, an exemplary method 350 comprises processing information regarding wireless links associated with two or more wireless communication subsystems 352, in this case Link 1, Link 2, and Link n, determining link status associated with transmissions made or attempted by each of the subsystems 354, and determining if there are any changes to the status of each link 356. Changes to a link status includes the link becoming intermittent or non-functional. Another status change includes a non-functional link becoming functional. Thus, boxes 354, as an example, make a determination of link status as being normal, intermittent, none-short duration, and none-long duration. Next the program determines whether there has been a change in a link status 356 from what was determined in boxes 354. If there has been a change, the method then moves to a determination of system status 358.

Examples of system status are "normal," "pump off body," "moving in/out of range," and "left behind." The system status determination 358 is then compared to the present system status an if a change is detected 360, a link recovery state is determined 362. If the system status change has been a return to a "normal" status, the processor may display a message to a user of "Normal status-all links active" or similar message. If however, a link has gone down and the system has moved to an alarm status, the method may then put the handheld controller into a power conservation mode in which it ceases monitoring certain links, or sets a time period in which it stops monitoring a particular link, such as ten minutes, but after that period has elapsed, the handheld may again check for the existence of the link. In the meanwhile, an alert is provided to the user. Also, the method moves to and then poll the down link again, such as a ten minute period.

Guidance is provided to the user 364 as a result of the steps discussed above. Examples are "none," "query to confirm pump inactive," "move controller closer to work area," "alarm," and "power conservation mode." If all links are operating normally and the system status is normal, the guidance to the user may take the form of "system normal" or other similar message, in one embodiment. However, if one link is down, the guidance may take the form of "keep the handheld on your person for the next ten minutes" or similar message. Other guidance is possible, such as check battery status in a device, or other.

Link status here may include various information regarding the wireless links set forth throughout this disclosure or otherwise known to an ordinary artisan, such as status or state of messages communication attempts, information regarding the wireless connections or protocols involved, etc., including whether the link is operating normally, whether the link is operating intermittently, status of short range transmissions, status of long range transmissions, bit error rate, and received signal strength, among other things.

Once status/information regarding the wireless links has been determined 354, the step of determining whether a change has occurred 356 is performed and includes utilizing or accessing logic (hardware, software, firmware, databases, etc.) that contains specific information regarding one or more of the wireless transmission protocols being used, the users, the transceiver units or their devices, the environments in which they will or are likely to be used, and/or other technical or wireless transmission details regarding transmission or usage of the devices. Such logic may, for example, include information regarding an interferer, a propagation characteristic, or a latency of the communications between the units. As used here, interferers may be, for example, objects that interfere with communications, other sources or causes of interference, co-channel users; and unintentional RF noise sources, etc. Propagation characteristics may be, for example, characteristics relating to signal performance, signal data, frequency, signal strength, receiver sensitivity, etc. And latency elements include, for example, factors relating to temporal aspects, arrival times, packet transmission rate, etc. In the case of a sensor 54 that has a latency of one minute, a link status change will not be noted until more than one minute has elapsed between transactions with the sensor. Even then, the processor of the handheld 70 may be programmed to permit five minutes to elapse before an alarm is raised concerning the glucose sensor 54. That is, a "system change" or issuing an alarm will not occur even though a "link status change" with the sensor has occurred, in this example. The same is possible for other occurrences relating to various system components.

Turning now also to FIG. 7, a chart some examples of system and link status are given. The rows R1 through R4 indicate the link status of one wireless device 400 while the columns C1 through C4 indicate the link status of another wireless device 410, both of which are communicating with a base station 110, which may take the form of the handheld device 70 discussed above. In the examples given, the glucose sensor is assumed to be continually attached to the user's body. The pump can be temporarily detached from the user's body. The controller can be left in another room or left at home. In the case of R1-C1, all is normal. In the case of R2-C1 where one device link status is "intermittent" while the link status of the other device is "normal," the diagnosis of the system may be that the user is moving in and out of range, but there is no need for a system change at this time. That is, the system continues to function without change. However the processor may cause an icon to be displayed on the screen indicating that an intermittent link with a particular device has been detected. Such a display is not considered to be a system change since the system continues to operate as before.

In the case of R3-C1, the situation labeled as "(1)" is found. In that case, a short duration interruption in a link exists but no system change is warranted again, because the logic may determine that this is possibly a normal case. Such a case often arises when the user is taking a shower and has placed the controller and pump together during that time. However, if the link status remains "none" for a "long duration," the chart moves to R4-C1, which is the situation labeled as "(2)," and an alarm is given. In this case, the link has been nonexistent for a "long" duration and action is recommended to the user.

Moving to the case of R4-C4, the situation of "(3)" is found. In this case where there has been no communication for a "long" duration, an audio alarm is not given. To save battery energy, the handheld does not try to link with the pump until the link with the sensor has been restored. The handheld thus makes a system change in that it monitors only one link now, i.e., the sensor link. Typically, once the user determines that he or she has left the controller behind, the user will retrieve the controller which will reestablish the sensor link. The controller will then switch the monitor system for the pump back on and will then reestablish that link.

Turning now to R1-C3 of FIG. 7, the situation labeled as "(4)" has been detected but no alarm is given. For a pump, the wait from short duration to long duration of no link may vary depending on how much insulin is in the pump and how long it takes to detect an occlusion, and if the basal rate changes (time of day). If the duration goes to R1-C4, which is a "long" duration, an alarm is given. In the case of R3-C3, which is indicated by "(5)," an alarm is not given. If nothing changes however, the state will either go to the cell to the right or the cell immediately below, both of which require that an alarm be given. Transitioning to R3-C4 or to R4-C3 depends on the definition of "long" as programmed. Such may be determined by reference to situation (3) above.

In the above-described embodiments, the system is event driven. Communicating or failing to communicate on each link is the driving event. Each link has its own schedule so the events are asynchronous. Each time a link status changes 356 (FIG. 6), the next level of logic looks to see if the change constitutes a system status change 358. For example, a link going from "normal" to "intermittent" is a Link Status Change 356 but may not be a System Status Change 358. If the system status changes 360, then two independent actions are possible. First, the link recovery state 362 may reconfigure a link device driver, for example, to completely disable one link. Second, the Diagnostics and Guidance 364 may alert the user, change a displayed icon, etc., to interact with the user. When a link status changes 356, the method executes the system status block 358 which could involve a table look-up, a sequence of case statements, or some other step to implement the logic.

Information, diagnoses, guidance and/or problem resolutions developed from these determinations may then, optionally, be provided to a user 364. Further exemplary determinations, here, may also include developing helpful feedback to users of the units, such as providing specific or individualized device status or device location information, diagnosis of, guidance regarding, or a resolution of a wireless-communication-related problem, and the like. Various examples of diagnosis; guidance, or resolution of identified problems are set forth throughout this disclosure and may include an "out of range" notification, a "vicinity" determination, a message regarding a device location or request to move a device, a message, regarding verification of a transmission or device detail, a recommendation regarding adjusting a transmission or device detail, a message to check for and/or avoid one or more likely causes of interference, a recommendation regarding a transmission or channel selection, among others.

Other exemplary logic and determination functionality may, with regard to units having Bluetooth enabled communications, include performing a Bluetooth channel usage/availability scan, wherein the information for provision to the user is determined based on results from the scan. According to these aspects, analysis of information derived from the scan is factored into the information determined for or provided to the user. For example, if one or more channels are determined to be in use, the method may recommend a different channel or use of a different transmission protocol. Further, if as a result of the scan the presence of a source of interference is identified, the method may again recommend use of a different protocol or some other means by which the identified interference can be avoided. Moreover, results from similar scans in wireless technologies other than Bluetooth may be used in a like fashion.

Referring back to FIG. 5, the base unit 110 in one implementation may also include a storage section such as a programmable, non-volatile memory device as part of the processor 116, or provided separately in the base unit 110, operatively coupled to the processor 116. The processor is further configured to perform Manchester decoding as well as error detection and correction upon the encoded data signals received from the transmitter unit 102.

In a further implementation, the one or more of the first unit 102, the base unit 110, the second unit 105, and/or the infusion section 109 may be configured to receive the blood glucose value wirelessly over a communication link from, for example, a glucose meter. In still a further implementation, the user or patient manipulating or using the analyte monitoring system 100 (FIG. 3) may manually input the blood glucose value using, for example, a user interface (for example, a keyboard, keypad, and the like) incorporated in the one or more of the first unit 102, the base unit 110, the second unit 105, or the infusion section 109.

In the present description, the terms "component," "module," "device," etc. may refer to any type of logical or functional process or blocks that may be implemented in a variety of ways. For example, the functions of various blocks can be combined with one another into any other number of modules. Each module can be implemented as a software program stored on a tangible memory (e.g., random access memory, read only memory, CD-ROM memory, hard disk drive); to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally; the modules can be implemented using special purpose instructions (SIMD instructions), field programmable logic arrays or any mix thereof which provides the desired level performance and cost.

As disclosed herein, implementations and features of the invention may be implemented through computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe components such as software, systems and methods consistent, with the innovations herein may be implemented with any combination of hardware, software and/or firmware. Moreover, the above-noted features and other aspects and principles of the innovations herein may be implemented in various environments. Such environments and related applications may be specially constructed for performing the various processes and operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types; e.g., metal-oxide semiconductor field-effect transistor ("MOSFET") technologies like complementary metal-oxide semiconductor ("CMOS"), bipolar technologies like emitter-coupled logic ("ECU), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) and carrier waves that maybe used to transfer such formatted data and/or instructions through wireless, optical; or wired signaling media or any combination thereof. Examples of transfers of such formatted data and/or instructions by carrier waves included but are not limited to, transfers (uploads; downloads, e-mail, etc.) over the Internet and/or other computer networks via one or more data transfer protocols (e.g., HTTP, FTP, SMTP, and so on).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using, the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Advantages of the system and method disclosed above include: 1) better ability to diagnose the cause of reduced radio performance; 2) better guidance to the user to improve radio performance, and 3) reduced power consumption which will extend battery life.

The Navigator® controller, when used on a combined product (CGM insulin pump remote control) can implement the logic to realize the benefits. Any dual radio system could benefit. For example, a Bluetooth-enabled cell phone could combine the status of the Bluetooth connection and cellular network connection to give better guidance to the user to improve the performance. Furthermore, different frequencies are not necessary in another embodiment. The same frequency could be used with the same protocol for different devices, but the wireless links would be different by means of particular data identifier as belonging to a particular link and device. An example of a two-link system that uses the same frequency and protocol is a hospital system that monitors two (or more) glucose sensors on two (or more) patients with one controller. The protocol differentiates the two glucose sensor signals by device ID (identification number). The status of each link can indicate the status of the system. For example, one patient is out of range while another patient is in range.

Other implementations of the invention will be apparent to those skilled in the art from consideration of the specification and practice of the invention disclosed herein. It is intended that the specification and examples be considered as exemplary only, with a true scope and spirit of the invention being indicated by the disclosure above in combination with the following paragraphs describing the scope of one or more implementations of the following invention.

What is claimed is:

1. A system of processing information regarding medical devices in wireless communication with each other, the system comprising:
    a base device having a first wireless communication link with a first medical device and a second wireless communication link with a second medical device; and
    the base device having a processor configured to monitor the status of the first wireless link and the status of the second wireless link;
    wherein the base device processor is further configured to determine if a problem exists with one or more of the first and second links; and
    wherein the base processor is further configured to compare the first wireless link status with the second wireless link status in the event that a problem with one or more of the monitored links is detected, and to provide guidance for resolving the problem based on the comparison.

2. The system of claim 1, wherein the processor is further configured to display the guidance on a visual display.

3. The system of claim 1, wherein the processor is further configured to determine that a link problem does not exist if the monitored link status lies within a latency of the respective medical device.

4. The system of claim 1, wherein the processor is further configured to cause a system change to occur based on the comparison.

5. The system of claim 4, wherein the processor is further configured to control the base device to cease monitoring a link based on the comparison, whereby power of the base unit is conserved.

6. The system method of claim 1, wherein the processor is further configured to make a determination of link status based on a selected time period and on at least one characteristic of the respective medical device.

7. The system method of claim 6, wherein the processor is further configured to issue an alarm based on the comparison and the selected time period.

8. The system method of claim 7, wherein the processor is further configured to extend the time period based on the comparison, before an alarm is provided.

9. The system of claim 1, wherein the processor is further configured to determine the status of at least one of the medical devices based on the link comparison.

10. The system of claim 1, wherein the processor is further configured to monitor the communication links to identify the existence of an intermittent communication link, and to consider the intermittent link in the comparison.

11. The system of claim 1, wherein:
    each of the medical devices are battery powered and the base station comprises a handheld battery-powered device; and
    the processor is further configured to initiate a system status change based at least in part on conserving battery power.

12. A method of processing information regarding a base station having a first wireless communication link with a first medical device and having a second wireless communication link with a second medical device, the method comprising:
    monitoring each communication link;
    detecting a problem in at least one of the communication links being monitored;
    determining if a problem exists with one or more of the monitored communication links;
    comparing the status of the monitored communication links with each other in the event that a problem appears to exist with one of the communication links; and
    providing guidance based on the link comparison for resolving the problem.

13. The method of claim 12, further comprising displaying the guidance on a visual display.

14. The method of claim 12, further comprising determining that a link problem does not exist if the monitored link status lies within a latency of the respective medical device.

15. The method of claim 12, further comprising changing the system status based on the comparison.

16. The method of claim 15, further comprising controlling the base device to cease monitoring a link based on the comparison, whereby power of the base unit is conserved.

17. The method of claim 12, further comprising making a determination of link status based on a selected time period and on at least one characteristic of the respective medical device.

18. The method of claim 17, further comprising issuing an alarm based on the comparison and the selected time period.

19. The method of claim 18, further comprising extending the time period based on the comparison, before an alarm is provided.

20. The method of claim 12, further comprising determining the status of at least one of the medical devices based on the link comparison.

21. The method of claim 12, further comprising monitoring the communication links to identify the existence of an intermittent communication link, and considering the intermittent link in the comparison.

* * * * *